United States Patent
Nies et al.

(10) Patent No.: US 12,352,719 B2
(45) Date of Patent: Jul. 8, 2025

(54) SOMATIC CELL-BASED ELECTRICAL BIOSENSOR

(71) Applicant: AVX Corporation, Fountain Inn, SC (US)

(72) Inventors: Craig W. Nies, Greenville, SC (US); Hari Kishan Rao Abbaraju, Simpsonville, SC (US)

(73) Assignee: KYCERA AVX Components Corporation, Fountain Inn, SC (US)

(*) Notice: Subject to any disclaimer, the term of this patent is extended or adjusted under 35 U.S.C. 154(b) by 71 days.

(21) Appl. No.: 17/024,811

(22) Filed: Sep. 18, 2020

(65) Prior Publication Data
US 2021/0088468 A1    Mar. 25, 2021

Related U.S. Application Data

(60) Provisional application No. 62/903,163, filed on Sep. 20, 2019.

(51) Int. Cl.
| | |
|---|---|
| *G01N 27/327* | (2006.01) |
| *C01B 32/158* | (2017.01) |
| *C01B 32/182* | (2017.01) |
| *C01G 7/00* | (2006.01) |
| *G01N 27/30* | (2006.01) |

(52) U.S. Cl.
CPC ......... *G01N 27/327* (2013.01); *C01B 32/158* (2017.08); *C01B 32/182* (2017.08); *C01G 7/00* (2013.01); *G01N 27/305* (2013.01)

(58) Field of Classification Search
CPC .............. G01N 27/327; G01N 27/305; G01N 33/5438; C01B 32/158; C01B 32/182; C01G 7/00
See application file for complete search history.

(56) References Cited

U.S. PATENT DOCUMENTS

| | | |
|---|---|---|
| 5,668,117 A | 9/1997 | Shapiro |
| 6,858,580 B2 | 2/2005 | Ansari et al. |
| 7,253,341 B2 | 8/2007 | Wang et al. |
| 7,638,283 B2 | 12/2009 | Krafft et al. |

(Continued)

FOREIGN PATENT DOCUMENTS

| | | |
|---|---|---|
| AU | 2012244075 | 11/2012 |
| AU | 2015201763 | 4/2015 |

(Continued)

OTHER PUBLICATIONS

Cho et al., English translation of KR20180122172A (Year: 2018).*

(Continued)

*Primary Examiner* — Luan V Van
*Assistant Examiner* — Shizhi Qian
(74) *Attorney, Agent, or Firm* — Dority & Manning, P.A.

(57) ABSTRACT

A biosensor having somatic cells immobilized on an electrode formed from a biologically inert material for sensing transepithelial/transendothelial electrical resistance is provided. The biosensor includes a working electrode formed from gold, graphene, carbon nanotube, or alloys or combinations thereof, having somatic cells formed directly thereon. With such a configuration, a very small sample size may be used while still eliciting an electrical response in the presence of a target composition.

10 Claims, 2 Drawing Sheets

(56) References Cited

U.S. PATENT DOCUMENTS

| | | |
|---|---|---|
| 7,727,511 B2 | 6/2010 | Siclovan et al. |
| 7,766,658 B2 | 8/2010 | Tricca et al. |
| 7,772,375 B2 | 8/2010 | Greferath et al. |
| 7,812,123 B2 | 10/2010 | Gurney et al. |
| 7,964,192 B1 | 6/2011 | Schenk |
| 8,067,222 B2 | 11/2011 | Kerovuo et al. |
| 8,128,930 B2 | 3/2012 | Acton et al. |
| 8,318,132 B2 | 11/2012 | Kolb et al. |
| 8,613,924 B2 | 12/2013 | Yokoseki et al. |
| 8,647,879 B2 | 2/2014 | Kim et al. |
| 8,673,579 B2 | 3/2014 | Orser et al. |
| 8,792,977 B2 | 7/2014 | Kakei et al. |
| 8,796,439 B2 | 8/2014 | Pfeifer et al. |
| 8,889,138 B2 | 11/2014 | Acton et al. |
| 9,090,679 B2 | 7/2015 | Yokoseki et al. |
| 9,156,814 B2 | 10/2015 | Yang et al. |
| 9,176,150 B2 | 11/2015 | Hillen et al. |
| 9,221,900 B2 | 12/2015 | Pfeifer et al. |
| 9,255,933 B2 | 2/2016 | Guo et al. |
| 9,309,309 B2 | 4/2016 | Gaspar et al. |
| 9,320,793 B2 | 4/2016 | Goure et al. |
| 9,365,419 B2 | 6/2016 | Haick et al. |
| 9,365,491 B2 | 6/2016 | Rishton et al. |
| 9,518,284 B2 | 12/2016 | Lindquist et al. |
| 9,688,734 B2 | 6/2017 | Hard et al. |
| 9,846,166 B2 | 12/2017 | Lim et al. |
| 10,030,065 B2 | 7/2018 | Brix et al. |
| 10,611,818 B2 | 4/2020 | Scholler et al. |
| 2004/0038333 A1 | 2/2004 | Randolph et al. |
| 2004/0048279 A1 | 3/2004 | Olek et al. |
| 2004/0152067 A1* | 8/2004 | Wang ............... G01N 33/48728 |
| | | 435/287.1 |
| 2004/0223909 A1 | 11/2004 | Montalto et al. |
| 2005/0031651 A1 | 2/2005 | Gervais et al. |
| 2005/0059634 A1 | 3/2005 | Venton et al. |
| 2005/0074763 A1 | 4/2005 | Wang et al. |
| 2005/0124016 A1 | 6/2005 | LaDu et al. |
| 2006/0135403 A1 | 6/2006 | Gervais et al. |
| 2006/0153801 A1 | 7/2006 | Ekwuribe et al. |
| 2007/0218499 A1 | 9/2007 | Lambert et al. |
| 2007/0264669 A1 | 11/2007 | Zhao et al. |
| 2008/0044356 A1 | 2/2008 | Lesne et al. |
| 2008/0113444 A1 | 5/2008 | Pray |
| 2008/0220449 A1 | 9/2008 | Vasan et al. |
| 2008/0305099 A1 | 12/2008 | Ahn et al. |
| 2009/0018218 A1 | 1/2009 | Krafft et al. |
| 2009/0062403 A1 | 3/2009 | McLaurin |
| 2009/0175894 A1 | 7/2009 | Golde et al. |
| 2009/0221431 A1 | 9/2009 | Yoo |
| 2009/0318825 A1 | 12/2009 | Kilborn |
| 2010/0028357 A1 | 2/2010 | Matsubara et al. |
| 2010/0048678 A1 | 2/2010 | Smit et al. |
| 2010/0070197 A1 | 3/2010 | Wang et al. |
| 2010/0093001 A1 | 4/2010 | Rousseau et al. |
| 2010/0152418 A1 | 6/2010 | Mutter et al. |
| 2010/0173828 A1 | 7/2010 | Hillen et al. |
| 2010/0200538 A1* | 8/2010 | Petisce ............... B81C 1/00539 |
| | | 216/13 |
| 2010/0221240 A1 | 9/2010 | Kapurniotu et al. |
| 2010/0234237 A1 | 9/2010 | Yoo |
| 2010/0240868 A1 | 9/2010 | Mach et al. |
| 2010/0291071 A1 | 11/2010 | Matsubara et al. |
| 2010/0291090 A1 | 11/2010 | Strittmatter et al. |
| 2010/0291097 A1 | 11/2010 | Pfeifer et al. |
| 2011/0070613 A1 | 3/2011 | Greferath et al. |
| 2011/0098309 A1 | 4/2011 | Look et al. |
| 2011/0098591 A1 | 4/2011 | Haick et al. |
| 2011/0244484 A1 | 10/2011 | Chae et al. |
| 2011/0294740 A1 | 12/2011 | Van Nostrand |
| 2011/0318380 A1 | 12/2011 | Brix et al. |
| 2012/0100129 A1 | 4/2012 | Gellerfors et al. |
| 2012/0156193 A1 | 6/2012 | Yokoseki et al. |
| 2012/0171216 A1 | 7/2012 | Pfeifer et al. |
| 2012/0177664 A1 | 7/2012 | Yokoseki et al. |
| 2012/0196935 A1 | 8/2012 | Schmid-Schonbein et al. |
| 2012/0270844 A1 | 10/2012 | Lichter et al. |
| 2013/0035579 A1 | 2/2013 | Le et al. |
| 2013/0059824 A1 | 3/2013 | Lichter et al. |
| 2013/0084283 A1 | 4/2013 | Cashman |
| 2013/0109581 A1 | 5/2013 | Salisbury et al. |
| 2013/0171066 A1 | 7/2013 | Sellergren et al. |
| 2013/0274437 A1 | 10/2013 | Duan et al. |
| 2013/0295095 A1 | 11/2013 | Bayer et al. |
| 2013/0345292 A1 | 12/2013 | Ewert et al. |
| 2014/0014536 A1* | 1/2014 | Weiss ................... G01N 27/327 |
| | | 205/792 |
| 2014/0141464 A1* | 5/2014 | Zantl ................. B01L 3/502769 |
| | | 435/29 |
| 2014/0155480 A1 | 6/2014 | Cruz et al. |
| 2014/0322731 A1 | 10/2014 | Krafft et al. |
| 2014/0378473 A1 | 12/2014 | Catalano et al. |
| 2015/0037826 A1 | 2/2015 | Willbold et al. |
| 2015/0183857 A1 | 7/2015 | Nicolau et al. |
| 2015/0285808 A1* | 10/2015 | Nagrath ........... G01N 33/54366 |
| | | 435/7.23 |
| 2016/0000891 A1 | 1/2016 | Barghorn et al. |
| 2016/0007874 A1* | 1/2016 | Ma ....................... A61B 5/6868 |
| | | 600/377 |
| 2016/0106691 A1 | 4/2016 | Ueda et al. |
| 2017/0172446 A1* | 6/2017 | Kuzum ................ A61B 5/0084 |
| 2017/0218058 A1 | 8/2017 | Rosenthal |
| 2017/0349554 A1 | 12/2017 | Catalano et al. |
| 2017/0349641 A1 | 12/2017 | Raskatov |
| 2017/0363646 A1 | 12/2017 | Llanes et al. |
| 2018/0194822 A1 | 7/2018 | McIntire |
| 2018/0238910 A1 | 8/2018 | Kang et al. |
| 2019/0025240 A1* | 1/2019 | Henry .................. G01N 27/305 |
| 2019/0210966 A1 | 7/2019 | Rishton et al. |
| 2019/0224474 A1* | 7/2019 | Yang ..................... A61B 5/4848 |
| 2020/0049689 A1 | 2/2020 | Maoz et al. |
| 2020/0071648 A1* | 3/2020 | Moore ...................... A61N 1/18 |
| 2020/0347114 A1 | 11/2020 | Scholler et al. |
| 2020/0348259 A1* | 11/2020 | Torsi .................. G01N 33/5438 |
| 2021/0009665 A1 | 1/2021 | Groves et al. |

FOREIGN PATENT DOCUMENTS

| | | | |
|---|---|---|---|
| AU | 2013202799 | 6/2016 | |
| AU | 2016204956 | 7/2018 | |
| CA | 2790433 | 5/2006 | |
| CA | 2598080 | 8/2006 | |
| CA | 2626783 | 5/2007 | |
| CN | 104277092 | 1/2015 | |
| CN | 107656084 A * | 2/2018 | |
| EP | 1379546 | 1/2004 | |
| EP | 2074145 | 7/2009 | |
| EP | 2170953 | 4/2010 | |
| EP | 2254592 | 12/2010 | |
| IN | 2492CHENP2009 | 7/2009 | |
| IN | 2905CHENP2010 | 11/2010 | |
| JP | 2007320934 | 12/2007 | |
| JP | 2008031099 | 2/2008 | |
| JP | 2008054511 | 3/2008 | |
| JP | 2016139492 A * | 8/2016 | |
| KR | 20110134720 A * | 12/2011 | |
| KR | 101609102 | 4/2016 | |
| KR | 20180122172 | 11/2018 | |
| KR | 20180122172 A * | 11/2018 | |
| MX | 2010000368 | 7/2010 | |
| MX | 2010000370 | 7/2010 | |
| NO | 20082288 | 5/2008 | |
| WO | WO-2004010103 A2 * | 1/2004 | ............ C12M 23/12 |
| WO | WO-2005098423 A1 * | 10/2005 | ............ B01L 3/5085 |
| WO | WO2006004824 | 1/2006 | |
| WO | WO2007049098 | 5/2007 | |
| WO | WO2009105123 | 8/2009 | |
| WO | WO2010037397 | 4/2010 | |
| WO | WO2012164476 | 12/2012 | |

(56) References Cited

FOREIGN PATENT DOCUMENTS

WO     WO2015181322     12/2015
WO     WO-2019166644 A1 *   9/2019     ........ B01L 3/502715

OTHER PUBLICATIONS

Van der Helm et al., Direct quantification of transendothelial electrical resistance in organs-on-chips, Biosensors and Bioelectronics, 85, 2016, 924-929. (Year: 2016).*

Sverdlijie K., Cell culture impedance sensing with thin film ITO electrodes, Master thesis, University of Oslo, Aug. 2016 (Year: 2016).*

Hemasiri et al., Fabrication of highly conductive graphene/ITO transparent bi-film through CVD and organic additives-free sol-gel techniques, Scientific Reports, 2017, 7, 17868 (Year: 2017).*

Singh et al., Voltaglue bioadhesives energized with interdigitated 3D-graphene electrodes, Advanced Healthcare Materials, 7, 2018, 1800538 (Year: 2018).*

Cui et al., English translation of CN-107656084-A, 2018. (Year: 2018).*

Zhen et al., Noncovalent monolayer modification of graphene using pyrene and cyclodextrin receptors for chemical sensing, ACS Applied Nano Materials, 2018, 1, 2718-2726 (Year: 2018).*

Gonzalez-Velasquez et al., "Soluble aggregates of the amyloid-b protein selectively stimulate permeability in human brain microvascular endothelial monolayers," Journal of Neurochemistry, 2008, pp. 466-477.

International Search Report and Written Opinion for PCT/US2020/051381 dated Jan. 4, 2021, 11 pages.

Kim et al., "Comparative analyses of plasma amyloid-b levels in heterogeneous and monomerized states by interdigitated microelectrode sensor system," Science Advances Apr. 17, 2019, 12 pages.

* cited by examiner

SOMATIC CELL-BASED ELECTRICAL BIOSENSOR

BACKGROUND OF THE INVENTION

Early detection and diagnosis are often critical factors in the treatment of terminal illnesses. However, many biomarkers are difficult to measure, or require expensive, time consuming, or invasive testing, such as cell counting, labeling and imaging, immunoassays, and fluorescence. One such disease that suffers from a lack of adequate testing for early diagnosis is Alzheimer's disease. Previously, transepithelial/transendothelial electrical resistance (TEER) sensing had been used to measure membrane potential and resistance of cerebral endothelial cells in a culture in order to detect biomarkers indicating early signs or Alzheimer's and other diseases.

Unfortunately, TEER apparatus utilize porous membranes and silver electrodes, making it difficult to immobilize cells on the electrode and requiring large sample sizes. For instance, existing TEER electrodes with silver electrodes are difficult to functionalize, as, likely due to underlying antimicrobial properties of the electrode material, the cells deposited for growth die instead of forming a confluent layer. Therefore, in order to sense the transepithelial/transendothelial electrical resistance using a TEER apparatus, cells are generally grown in vitro in a well to form a monolayer. TEER sensor electrodes would then be inserted into the well, on either side of the monolayer, to measure the resistance of the monolayer. Then, a sample would be introduced to the well, and the TEER sensor electrodes would again be placed on either side of the monolayer in order to measure any change in the electrical resistance of the cells after introduction to the sample. This procedure requires four electrodes, two working electrodes and two reference electrodes, in order to sense the change in resistance across the monolayer. Furthermore, as the sample needs to be combined with the cells prior to measurement, the method and sensor required a large volume of sample, which is problematic when the sample is a valuable or limited sample, such as a biopsy, blood serum, or spino-cerebral fluid, as generally, only small volumes of sample are available. As such, a need exists for a biosensor that solves one or more of the above problems.

SUMMARY OF THE INVENTION

The present disclosure may generally be directed to a biosensor for detecting transepithelial/transendothelial electrical resistance. The biosensor includes at least one substrate, a working electrode formed on at least a portion of the at least one substrate that includes a biologically inert material, and a reference electrode formed on the at least one substrate, where somatic cells are immobilized on at least a portion of the working electrode. The biosensor is configured to detect a first resistance measurement and a second resistance measurement, where the somatic cells are immobilized on the working electrode during both the first resistance measurement and the second resistance measurement.

The present disclosure may also be generally directed to a method of detecting a change in transepithelial/transendothelial electrical resistance of somatic cells. The method includes providing a biosensor having at least one substrate, a working electrode formed on at least a portion of the at least one substrate that includes a biologically inert material, and a reference electrode formed on the at least one substrate, where somatic cells are immobilized on at least a portion of the working electrode. The method also includes conducting a first resistance measurement by measuring the voltage at the working electrode across the somatic cells, contacting the working electrode with a biological sample, and conducting a second resistance measurement by measuring the voltage at the working electrode across the somatic cells.

Other features and aspects of the present invention are set forth in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figure in which.

Figure 1A:
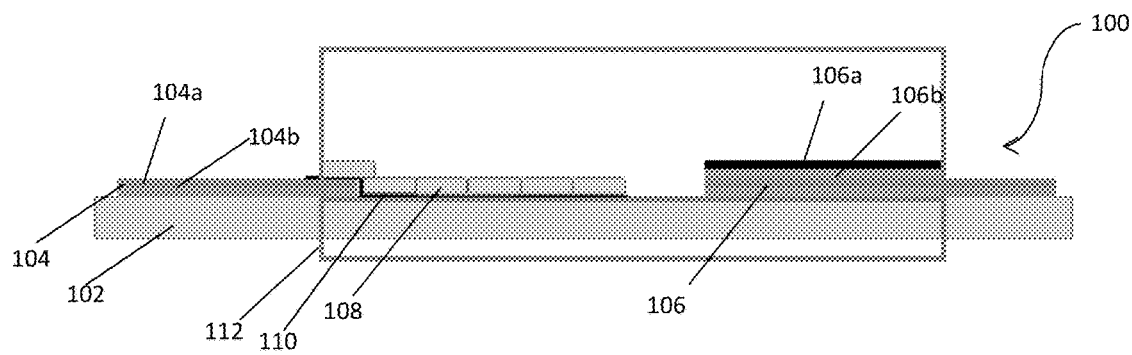
FIG. 1A illustrates a schematic side view of a TEER biosensor according to the present disclosure.

Repeat use of reference characters throughout the present specification and appended drawings is intended to represent same or analogous features, elements, or steps thereof.

DETAILED DESCRIPTION OF THE INVENTION

It is to be understood by one of ordinary skill in the art that the present discussion is a description of exemplary embodiments only, and is not intended as limiting the broader aspects of the present invention, which broader aspects are embodied in the exemplary construction.

Generally speaking, the present invention is directed to a biosensor having somatic cells immobilized on at least one working electrode, where the working electrode is formed from a biologically inert material. Due to this unique configuration, the biosensor is able to sense the presence of a target composition by detecting a change in the transepithelial/transendothelial electrical resistance (TEER) of the somatic cells immobilized on the surface of the working electrode when the working electrode is contacted with a sample containing the target composition. Therefore, a TEER biosensor according to the present disclosure may be formed that does not require the use of a solution containing a cell monolayer. Instead, somatic cells may be formed directly on the working electrode and contacted with a sample that is suspected to contain a target composition.

Furthermore, due to this unique configuration, the present inventor has found that a TEER biosensor formed according to the present disclosure may be highly selective and accurate at sensing the presence of a target composition even when only a small volume of sample is used. For instance, the TEER biosensor according to the present disclosure may be capable of detecting a target composition in a sample having a volume of about 1 µL to about 500 µL, such as about 10 µL to about 250 µL, such as about 15 µL to about 100 µL, such as about 25 µL to about 75 µL.

Various embodiments of the biosensor will now be described in more detail.

As discussed above, in one aspect, a TEER biosensor according to the present disclosure includes at least one working electrode. The working electrode is formed from a biologically inert material. Meaning, the working electrode for a TEER biosensor according to the present disclosure is formed from a material that supports or maintains the somatic cells when immobilized on the working electrode. For instance, in one aspect, the working electrode may be formed from a metal, a semi-conductor, an oxide, a carbon, a polymer, or alloys or combinations thereof. By way of example, the working electrode material may be gold, platinum, doped silicon, tin oxide, titanium dioxide, graphene oxide, graphite, fullerenes, graphene, conductive polymers having doped polyaniline, undoped polyaniline, polypyrrole, and/or polythiophene. Of course, the polymer may be conductive or semi-conductive via addition of conducting or semi-conducting species, such as nanoparticles and/or carbonaceous elements, such as carbon black, graphite, carbon nanotubes, fullerenes, graphene, or a combination thereof.

In one aspect, the working electrode is formed from a biologically inert material that is also generally transparent. For instance, in one aspect, the working electrode may be formed from a biologically inert material have a % transmittance (visible spectrum) of from about 60% to about 99.9% measured using a conventional color meter spectrophotometer. The light transmittance is expressed as a percentage and determined using the following formula: Light Transmittance=(100−Percent Opacity). Thus, a material having a percent opacity of 70% has a light transmittance of 30%. In one aspect, graphene may be used as a biologically inert material that is also generally transparent, to form the working electrode. A generally transparent working electrode may allow the somatic cell growth and reaction to the sample to be observed in conjunction.

The TEER biosensor also includes at least one reference electrode. The working electrode and the reference electrode may be selected to be formed the same or different materials. For instance, in one aspect, both the working electrode and the reference electrode may be formed from a biologically inert material. However, in an alternative aspect, the reference electrode may be formed from any electrode material known in the art. Furthermore, in one aspect, the reference electrode may be formed from silver, silver chloride, or alloys or combinations thereof. Nonetheless, the reference electrode is selected from a material that is capable of delivering a current, such as a direct current (DC) or alternating current (AC) voltage signal. For instance, as generally known in the art, the reference electrode is selected and formed so as to form a stable voltage at the interface during the time of the measurement. An Ag/AgCl reference is therefore often used for that reason.

In a further aspect, the TEER biosensor according to the present disclosure may include at least two working electrodes and at least two reference electrodes. Particularly, while not necessary, a four-electrode assembly may allow further improvements to electrical performance and measurements, as, by separating the current passing and voltage measuring electrodes, contact and lead resistances, including electrode and solution interfacial resistances, may be reduced or removed. Therefore, in such a configuration, instead of having both electrodes be both current-passing and voltage-measuring, two electrodes operate as current-passing electrodes, and two electrodes operate voltage measuring electrodes. However, as discussed above and in greater detail below, in one aspect, only two electrodes are used.

Nonetheless, the working electrode, the reference electrode, or both the working electrode and reference electrode, may be formed as a freestanding electrode, or may be applied over a substrate. For instance, a working electrode layer and/or a reference electrode layer may be formed on all, or at least a portion of a substrate. In one aspect, the working electrode layer and/or reference electrode layer may cover substantially all of sensing region located on a first end of the substrate opposite a second end from which an electrical contact, if used, extends, which will be discussed in greater detail below. Therefore, in one aspect, about 1% to about 50%, such as about 5% to about 45%, such as about 10% to about 40%, or such as about 12.5% to about 35% of the substrate may have an electrode layer applied thereon.

Of course, while the reference electrode may have a size that is the same or similar to the working electrode, in one aspect, the reference electrode has a size of about 1 mm² to about 100 mm², such as about 1.5 mm² to about 50 mm², such as about 1.75 mm² to about 10 mm², such as about 2 mm² to about 5 mm².

While the working electrode and/or reference electrode may be patterned or unpatterned, the electrode material that forms the working electrode and/or reference electrode may be applied to the substrate via screen printing, vapor deposition, sputtering, electroplating, photolithography, metal lift-off, a transfer process, and laser ablation. As discussed above in regards to the size of the electrodes, the working electrode and reference electrode may be formed from the same or different application processes.

Regardless of the manner of application, the working or reference electrode material may be applied to the substrate such that at least a portion of the working or reference electrode has a thickness of from about 0.3 nanometers (nm) to about 500 nm, such as about 10 nm to about 400 nm, such as from about 20 nm to about 200 nm, such as from about 25 nm to about 100 nm. The electrode material may be applied to the substrate in a single layer, or multiple layers, each having any of the above thicknesses, or may be formed from two or more layers having a total combined thickness within the above ranges. Moreover, the working electrode and reference electrode may have the same or different thicknesses according to the above ranges, and may have the same or different number of layers.

While the working electrode and reference electrode according to the present disclosure may exhibit good adherence to the substrate, in one aspect, an adhesion layer may be used between the substrate and the electrodes. Adhesion layers include, but are not limited to, Ta, Cr, TaN, TiW, Ti, TiN. In one aspect, the working electrode or reference electrode may be formed directly over the substrate and no adhesive layer may be used. In a further aspect, two or more adhesive layers may be used. In such as aspect where two or more adhesive layers are used, one of the layers may include a gold layer. Additionally or alternatively, in an aspect with two or more adhesive layers, a gold layer may be disposed above or between a TiW layer. However, it should be understood that, in one aspect, gold may only be used as part of the working electrode. Furthermore, it should be understood that, in one aspect, no adhesive layer is used, and the working electrode and/or reference electrode is disposed over the substrate.

While any electrode material, application method, and thickness may be selected, in an aspect that includes a substrate, a substrate may be transparent or opaque, and formed from one or more layers. The substrate may be generally flat and/or continuous, or may be etched or otherwise patterned. For instance, in one aspect, each layer may be prepared by numerous techniques including laser ablation, plasma etching, wet chemical methods, injection molding, or press molding. Regardless of the manner of application, the substrate may have a thickness of about 0.1 mm to about 1 mm, such as about 0.2 mm to about 0.8 mm, such as from about 0.3 mm to about 0.7 mm. Of course, as discussed above in regards to the electrode layers, each layer may have a thickness according to the above ranges, or the total thickness of all of the layers may have a thickness according to the above discussed ranges.

Notwithstanding the thickness or number of layers, in one aspect, the substrate may be formed from a polymer, glass, quartz, a thermoplastic, a thermoset resin, or a silicone. For instance, in an aspect, the substrate may be formed from glass, quartz, silicone, silicon nitride, silicone elastomer, polydimethylsiloxane, polycarbonate, styrene-ethylene/butylene-styrene, polyurethane, polyester, an epoxy-based photoresist, polymethylmethacrylate, polyvinyl chloride, polystyrene, polyimide, polyethylene terephthalate, cellulose acetate or combinations thereof. In one aspect, the substrate may be formed from glass, quartz, or silicone.

As will be discussed in greater detail below, in one aspect, the substrate may be a single substrate having both the working electrode and reference electrode formed thereon in a spaced-apart manner. However, it should be understood that the working electrode substrate and reference electrode substrate, may instead be completely separated, such that the working electrode is formed on a first substrate and the reference electrode is formed on a second substrate. Furthermore, in another aspect, the substrate may be partially connected, such that only an edge region opposite the sensing region where the working electrode and reference electrode are formed may be connected, and otherwise, may have a gap or void separating the portion of the substrate that the working electrode and the portion of the substrate that the reference electrode are formed thereon.

Nonetheless, in one aspect, the working electrode, the reference electrode, or both the reference electrode and the working electrode are connected to electrical contacts for coupling to a measuring device. The electrical contacts may be integrated into a substrate, in a permanent connection, such as will be discussed in greater detail below, or may be otherwise temporarily electrically connected to the working electrode and/or reference electrode. In an aspect where an electrical contact is used, the electrical contact may be integrated into the substrate along a length of the substrate body, and extend beyond the substrate at a location remote, or opposite from the sensing region/electrode. For example, in an aspect where the substrate may have a quadrilateral or rectangular shape, the working electrode/reference electrode and sensing region may be adjacent to a first end of the substrate. The electrical contacts may extend across the length of the substrate body, contacting the working electrode and/or reference electrode, and then extend beyond a second end of the substrate, in a direction opposite from the first end. In such a manner, the electrode/sensing region may be easily contacted with a sample, or inserted into a sample, while being connected to a measuring device.

After formation of the working electrode, the working electrode may be functionalized with the desired somatic cell(s). As discussed above, a TEER biosensor according to the present disclosure is well suited to functionalization with somatic cells. Thus, the TEER biosensor may be useful for detecting changes in cells, or cell layers, that are susceptible to being altered or damaged by a target composition. For instance, somatic cells according to the present disclosure may be endothelial or epithelial cells from the spino-cerebral system, the lymphatic system, the gastrointestinal system, the pulmonary system, the respiratory system, the digestive system, the urinary system, the reproductive system, the central nervous system, as well as other systems that may suffer damage or disease due to changes in the epithelial or endothelial barrier. As discussed above, the TEER biosensor according to the present disclosure may operate by growing somatic cells, such as a somatic cell layer, on a working electrode, and introducing a sample that is suspected may contain a target composition that may cause a change in the electrical properties of the somatic cells, to the working electrode. Therefore, it should be understood that somatic cells from other systems may be used to form the somatic cell layer over the working electrode when it is desired to test for the presence of a target composition specific to a type of somatic cells, or a target composition that affects more than one bodily system. However, in one aspect, the TEER biosensor according to the present disclosure may be well suited for detecting Alzheimer's disease or Kidney disease, and thus, may utilize spino-cerebral cells or urinary system cells, and, in one aspect, may be used to detect Alzheimer's disease and utilize spino-cerebral cells.

In one aspect, a target disease may be Alzheimer's. In such an aspect, mammalian brain microvascular endothelial cells, or more generally, spino-cerebral endothelial cells, may be selected as the somatic cells and grown on a working electrode according to the present disclosure. After formation of the cell layer on the working electrode, the working electrode may be contacted with a sample that is suspected to contain soluble oligomers of amyloid-β protein (AβO) or higher than normal levels of the soluble AβO, which is the target composition in this example. Particularly, it has been found that soluble AβO increases the permeability, and alters tight junctions, of spino-cerebral endothelial cells, allowing the fibrillar form of the amyloid proteins to cross the blood-brain barrier and create damaging deposits that have been linked to Alzheimer's disease. Therefore, in this example, as soluble AβO operates by decreasing the resistance and increasing the permeability of spino-cerebral endothelial cells, if an amount, or an above average amount of soluble AβO, is present in the sample, the electrical resistance of the endothelial cells immobilized on the working electrode would be decreased. This would cause a corresponding decrease in the TEER measurement measured by the TEER biosensor according to the present disclosure, indicating the presence of an Alzheimer's biomarker.

Notwithstanding the disease or type of somatic cells selected, in one aspect, the target composition may be amyloid-β protein (Aβ), soluble AβO, inflammatory agents such as IL-22, and Claudin-2, cancer cells, asymmetric dimethylarginine, symmetric dimethylarginine, as well as others that may be known in the art. Regardless of the desired target composition, the target composition may be contained in a sample of mammalian blood, serum, spinal fluid, tissue, bone marrow, or other matter, based upon the target system. In one aspect, however, the sample is mammalian blood or serum, and in an aspect, the sample is human blood or serum.

Notwithstanding the somatic cells selected, the somatic cells are functionalized or immobilized on an electrode using any growth method as may be known in the art. For instance, in one aspect, selected somatic cells, such as an endothelial or epithelial cell line may be combined with a buffer solution such as a phosphate saline solution, and seeded on an electrode. The working electrode may either have a growth medium applied thereto, or the buffer/cell solution may include an extracellular growth medium. For instance, in an aspect, the extracellular growth medium may include a glycoprotein, a gelatin, a protein, or combinations thereof. In one aspect, the extracellular growth medium may include two or more of collagen, fibronectin, and gelatin. Notwithstanding the extracellular growth medium selected, the extracellular growth medium may be applied at a concentration of about 1 μg/mL to about 100 μg/mL, such as about 10 μg/mL to about 90 μg/mL, such as about 20 μg/mL to about 80 μg/m L, such as about 30 μg/mL to about 70 μg/m L.

In one aspect, the somatic cells may be seeded at a density of $5\times10^3$-$6\times10^7$ cells/mL and incubated until the desired concentration has been reached, or until confluence has been obtained. The extracellular growth medium may be replaced as needed until the desired concentration or confluence is reached. For instance, in one aspect, cell confluence may be detected due to a spike in resistance exhibited by the immobilized somatic cells, or may instead be determined based upon the resistance of the cell layer. In regards to blood-brain barrier cells, such as spino-cerebral endothelial cells, the resistance at confluence may be about 550 $\Omega$*$cm^2$, of which measurement and determination of will be discussed in greater detail below, but, of course, it should be acknowledged that differing cell types exhibit a different resistance at confluence, as is known in the art. Nonetheless, the cell confluence may be used to determine that the cell culture has properly grown over the working electrode, and may also be used as a baseline resistance value for the TEER biosensor. Of course, as may be known in the art, desired cell concentration or confluence may also be confirmed by other methods, such as an optical impedance determination. Alternatively, the somatic cells may be applied to the working electrode at discrete locations via contact printing, inkjet printing or photolithographical synthesis.

In one aspect, the somatic cells are immobilized on the working electrode before, during, or after, seeding and incubation. Particularly, in an aspect the immobilizing agent may be a self-assembling monolayer (SAM). The monolayer may be formed of monomer units of a hydrocarbon including cyclic and polycyclic hydrocarbons, a thiol, a diazonium, an azide, a disulfide, a sulfide, a sulfonic acid, an isocyanide, a siloxane, a silicone, including sol-gels, a phosphate, or combinations or derivatives thereof. For instance, in one aspect, the SAM may be formed from monomer units of a thiol, pyrene, diazonium, azide, a sol-gel, such as TMOS or TEOS, or combinations thereof. In one aspect, the immobilizing agent for a metal electrode, such as a gold electrode, may be different than an immobilizing agent for a carbon based, oxide, based, or polymer based electrode, such as graphene or carbon nanotube electrode. In such an aspect, a thiol is used with a metal electrode and a pyrene, a diazonium, an azide, or combinations thereof are utilized with a carbon based, oxide, based, or polymer based electrode. Of course, it should be understood that any of the discussed linking agents, or others as are known in the art, may be used with either electrode.

Regardless of the monomer unit selected to form the SAM, in one aspect, the monomer is applied to the surface of the working electrode, either alone, or in the presence of a linking aid. For instance, as may be known in the art, sulfur based compounds may readily polymerize in the presence of metal electrodes, however, carbon based or polymer based electrodes may benefit from the addition of a immobilizing aid, such as by introducing free hydroxy groups, a peroxide, lithium, a Grignard reagent, metal oxides, or combinations thereof.

Nonetheless, after introduction and optional exposure to the immobilizing aid, the monomer may be allowed to polymerize on the working electrode surface using a variety of well-known techniques. For example, the monomer, immobilizing agent, and any other additives may be directly immobilized on the surface of the working electrode, may be contained within a substrate that is disposed on the surface of the electrode, may be mixed into the materials used to form the working electrode, and so forth. In one embodiment, the monomer, immobilizing agent, and any other additives are formulated into a solution and screen-printed, ink-jet printed, drop coated, or sprayed onto the working electrode surface. Nonetheless, after introduction and optional exposure to the immobilizing aid, the monomer may be allowed to polymerize on the working electrode's surface. After polymerization, the immobilizing aid may bind the somatic cells to the working electrode, immobilizing the somatic cells on, or adjacent to, the working electrode's surface.

After the immobilizing agent, and optionally the immobilizing aid, have secured the somatic cells to the working electrode, a TEER biosensor according to the present disclosure may be used to measure resistance values, in $\Omega$*$cm^2$ of the baseline resistance of the somatic cell monolayer, as well as any change in resistance exhibited by the somatic cells, upon exposure to a sample. As may be known in the art, TEER reflects the resistance to ion diffusion across a cell monolayer. Therefore, TEER takes into account total resistance of the system, as well as the area of the system. For instance, TEER values ($\Omega$*$cm^2$) may be determined by subtracting the baseline resistance value measured prior to the introduction of a sample, and then multiplying the resistance value ($\Omega$) by the cell culture surface area ($cm^2$), as is known in the art. The baseline resistance value measured in the absence of sample are subtracted from results obtained after introducing the TEER biosensor to a sample, and specific TEER values are determined by multiplying the specific resistance times the total cell culture surface area on the PDMS membrane.

Generally, the resistance, also referred to as the ohmic resistance, may be determined by the following method. Particularly, a biosensor according to the present disclosure may be contacted with a sample suspected to contain a target compound. A reference electrode is used to provide an alternating current (AC) voltage signal to the sample, and the resistance, and, the change in resistance, of the somatic cell layer on the biosensor is measured by detecting the change in voltage, if any, across the somatic cell layer on the working electrode, after the working electrode is contacted with the sample. Particularly, as may be known in the art, ohmic resistance is calculated based on Ohm's law as a ratio of the voltage and current, and thus, any changes in voltage may be used to determine the change in resistance of the somatic cells. When conducting the measurements, the AC voltage signal may have a frequency of about 12.5 Hz, and the measurement is made at a temperature selected based upon the growth medium and temperature of the selected cell culture as is known in the art. However, in one aspect, a central measurement system, such as a voltmeter, may be connected to the working electrodes and used to detect any changes in voltage.

Regardless of the method of measuring, and as discussed above, the biosensor may be introduced to a sample suspected of containing a target composition. Of course, as there is no need to place the somatic cells and sample into a solution, as in the prior art, in one aspect, a small volume of sample may simply be applied to the working electrode and reference electrode of the biosensor. Alternatively, the TEER biosensor may be introduced to a well as is known in the art, but again, the sample size may be decreased as the somatic cells are already immobilized on the working electrode.

Moreover, in a further aspect, the sample may be introduced to the biosensor in a case that surrounds at least the sensing portion of the working electrode and reference electrode. For instance, in one aspect, a case may be formed of a rigid, nonconductive polymer. In one aspect the polymer may be a thermoplastic, a polystyrene, a polycarbonate, a polyethylene, or copolymers or combinations thereof, as well as other materials known in the art. The case may completely encapsulate the biosensor, leaving only a portion of the electrical traces protruding from the case wall, or may instead only partially encapsulate the biosensor such that a portion of the substrate(s) also protrudes from the case. Furthermore, in one aspect, the case may contain slots such that the working electrode and reference electrode may be inserted into the case in a releasable manner.

The case may generally have a quadrilateral or rectangular shape. But of course, it should be understood that any shape casing may be selected based upon the size and shape of the working electrode and reference electrode. Therefore, in one aspect, the case has an upper and lower wall and four side walls. In one aspect the substrate(s) and the case may have a longest dimension of about 5 inches or less, such as about 4 inches or less, such as about 3 inches or less, such as about 2 inches or less, such as about 0.5 inches or greater, or such as about 0.5 inches to about 1 inch. Furthermore, the case may have a size in a width direction of about 2.5 inches or less, such as about 2 inches or less, such as about 1.5 inches or less, such as about 1 inch or less, such as about 0.25 inches or greater, or such as about 0.25 inches to about 0.75 inches. Additionally or alternatively, the case may have a thickness or height of about 2 inches or less, such as about 1.5 inches or less, such as about 1 inch or less, such as about 0.5 inches or less, such as about 0.1 inches or greater, or such as about 0.1 inches to about 0.25 inches. In such an aspect, the substrate(s) may be inserted into the case such that the longest dimension of the substrate(s) is perpendicular to the longest direction of the case. Of course, the case and substrates may have different relative geometries based upon the shape and size of the working electrode and reference electrode.

In one aspect, the case also includes at least one inlet and/or at least one outlet. The inlet(s) and outlet(s) may have a tapered, conical shape, such that the outermost part of the inlet(s) and outlet(s) has a larger diameter than the innermost part of the inlet(s) and outlet(s). Of course, in one aspect, the inlet(s) and outlet(s) may simply have a cross-section that is consistently sized along the entirety of the case wall. In such an aspect, the cross-section may be square, circular, rectangular, triangular, or any other shape as known in the art. It should also be understood that the additional cross-sections may also have a tapered geometry as discussed above.

Moreover, in one aspect, the case may also include a channel that generally extends between at least one inlet and at least one outlet. The channel may have a diameter and length sized to encourage fluid flow from the inlet to the outlet, while contacting the biosensor for an amount of time sufficient to provide a proper resistance measurement. Particularly, in an aspect, the channel contacts at least a sensing portion of the working electrode and sensing electrode, so as to bring a sample introduced via an inlet(s) into contact with the working electrode and reference electrode. For instance, in one aspect, the channel may have a diameter and length so as to have a volume of about 300 microliters or less, such as about 250 microliters or less, such as about 200 microliters or less, such as about 150 microliters or less, such as about 100 microliters or less, such as about 50 microliters or less, such as about 30 microliters or less, such as about 1 microliter or greater, or such as about 10 microliters to about 50 microliters.

Of course, while the case has been discussed in detail, it should be understood that, as discussed above, in one aspect, the TEER biosensor may instead have a chopstick orientation as is known in the art. However, unlike traditional chopstick electrodes, the TEER biosensor according to the present disclosure may only require a single electrode and a single reference electrode, instead of the two-pair system as generally used. Particularly, as discussed above, as the somatic cells are grown on the surface of the working electrode, it is not necessary to place measurement electrodes on either side of a monolayer in solution. Therefore, unlike the prior art chopstick electrodes, the TEER biosensor may provide results based upon the change in resistance of the somatic cells growing on the working electrode, and thus, only require a single pair of electrodes.

Figure 1B:
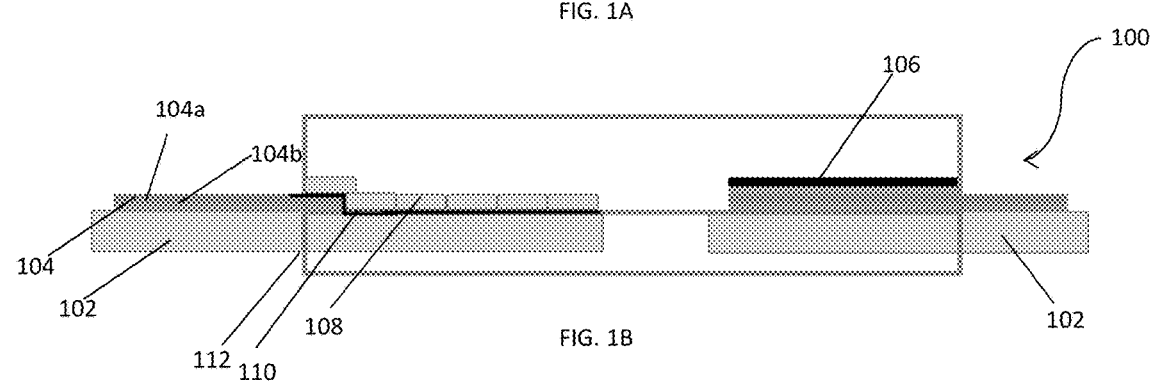
FIG. 1B illustrates a schematic side view of a TEER biosensor according to the present disclosure.

Nonetheless, a TEER biosensor according to the present disclosure may be further understood by referring to FIGS. 1A and 1B. For instance, FIGS. 1A and 1B may generally show a TEER biosensor 100 that includes a substrate 102, an electrode 104, a reference electrode 106, and somatic cells 108. As shown in FIGS. 1A and 1B, the working electrode 104 and reference electrode 106 may be located on the same substrate 102 (FIG. 1A) or separate substrates 102 (FIG. 1B). Of course, while FIGS. 1A and 1B generally show the TEER biosensor 100 as having the working electrode 104 and reference electrode 106 on opposite ends of the biosensor 100, it should also be understood that the working electrode 104 and reference electrode 106 may be located substantially parallel to each other (shown more fully in FIGS. 2-4), or across from each other (not shown), as may be generally known as a "chopstick" arrangement.

Regardless of the configuration used, in one aspect, the TEER biosensor according to the present disclosure includes a substrate 102 as discussed above. For instance, in one aspect, the substrate is a polymer, glass, or a silicon. In an aspect, the substrate may be a rigid substrate formed from glass. Of course, as discussed above, it should be understood that other substrates as are known in the art may be used.

Notwithstanding the substrate selected, an electrode 104 and a reference electrode 106 may be formed on the substrate. As previously discussed, the working electrode 104 may be formed from a material selected to be biologically inert. In one aspect, the electrode is a gold electrode. Additionally or alternatively, the working electrode 104 is formed from graphene. In some aspects, graphene may be desired due to its transparency, allowing the samples to be observed during measurement.

As discussed above, the reference electrode 106 may be formed from the same material or a different material than the working electrode 104. For instance, the reference electrode 106 may also be formed from gold, graphene, or carbon nanotube, or may be formed from platinum, iridium, titanium, silver, iridium oxide, rhodium, rhodium oxide, tantalum, titanium nitride, niobium and any alloys thereof.

Regardless of the material used to form the reference electrode, the reference electrode 106 may be spaced apart from the working electrode 104 in at least one direction (X, Y, and/or Z), and, as discussed above, may be located on the same substrate 102, or a different substrate 102, than the working electrode 104.

As discussed above, while the working electrode and reference electrode according to the present disclosure may exhibit good adherence to the substrate, in one aspect, an adhesion layer may be used between the substrate and the electrodes. For instance, as shown in FIGS. 1A and 1B, the working electrode 104 may be formed from an electrode layer 104a disposed above an adhesive layer 104b. Of course, as discussed above, in one aspect, the electrode layer 104a may be formed directly over the substrate and no adhesive layer may be used. Similarly, the reference electrode 106 may include a reference electrode layer 106a that may be disposed over one or more adhesive layers 106b. In one aspect, the one or more adhesive layers 104b and/or 106b may include a gold layer disposed above or between a TiW layer, however, it should be understood that, in one aspect, gold may only be used as part of the working electrode. Furthermore, as discussed in regards to electrode 104, it should be understood that, in one aspect, no adhesive layer is used, and the working electrode is disposed over the substrate 102.

Regardless of whether an adhesive layer is used, the somatic cells 108 may be immobilized on the working electrode 104. For instance, the somatic cells 108 may be grown as is known on the art in order to form a layer of cells over all or a portion of the working electrode 104. Regardless of the method of growth, the somatic cells may be tested to ensure that the desired confluency has been achieved or to ensure that the somatic cells contain the proper baseline for the selected somatic cell type. For instance, in regards to the Alzheimer's example above, the chosen somatic cells are spino-cerebral endothelial cells, which may be tested, after growth, such as by a permeability assay, to ensure that the cells exhibit adequate resistance and permeability prior to introduction of a sample to the cells.

The somatic cells may be immobilized on the working electrode 104, either prior to or during growth of the somatic cell layer, utilizing one or more linking agents 110 as discussed above. For instance, in one aspect, the linking agent 110 may be a thiol, pyrene, diazonium, azide, a sol-gel, such as TMOS or TEOS, or combinations thereof. In one aspect, the linking agent 110 for the gold electrode may be different than a linking agent 110 for a graphene or carbon nanotube electrode. In such an aspect, a thiol is used with a gold electrode and a pyrene, a diazonium, an azide, or combinations thereof are utilized with the graphene or carbon nanotube electrode. Of course, it should be understood that any of the discussed linking agents, or others as are known in the art, may be used with either electrode.

Furthermore, as shown in FIGS. 1A and 1B, the TEER biosensor may also optionally include a case 112 which surrounds the portion of the working electrode 104 and reference electrode 106 to be contacted by a sample. The case 112 may have any shape or size as is known in the art, and may be formed from a standard material such as an unreactive plastic that allows for assembly and disassembly of the case. But, it should be understood that, in one aspect, the case is formed from a single piece, and access and removal of the sample may only be through one or more ports, which are described more fully below. Of course, in one aspect, the TEER biosensor does not include a casing, and instead, the working electrode 104 and reference electrode may be inserted into a reservoir or container that holds the sample to be tested (not shown).

While not shown, it should be understood that the biosensor 100 may be connected via the working electrode 104 and reference electrode 106 to a central device that provides a current to the reference electrode 106, and which measures any change in voltage experienced by the working electrode 104. The device may provide an output of the change in voltage to a user. It should be understood that any central device as known in the art may be used with the biosensor according to the present disclosure.

Figure 2A:
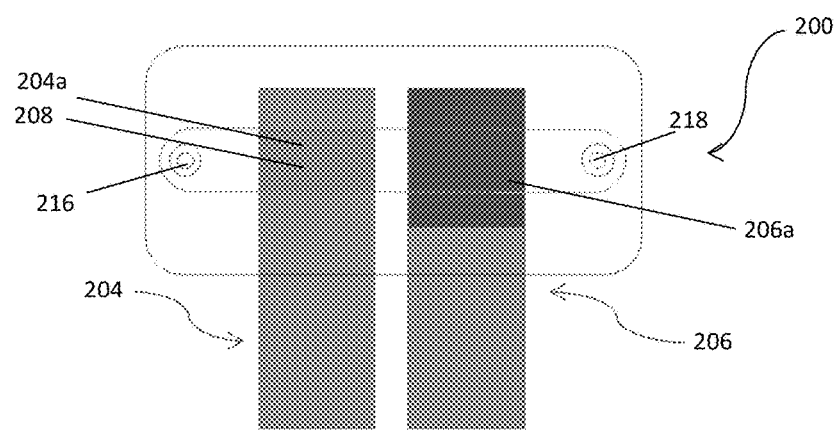
FIG. 2A illustrates a top view of a TEER biosensor according to the present disclosure.
Figure 2B:
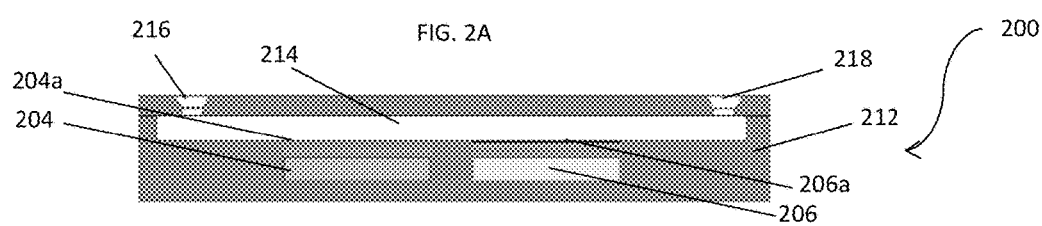
FIG. 2B illustrates a cross-section of the TEER biosensor of FIG. 2A.

Referring now to FIGS. 2A and 2B, which illustrate a further aspect according to the present disclosure, a biosensor 200 includes an electrode 204 and a reference electrode 206, both of which have a sensing region 204a and 206a, respectively, located in contact with a channel 214 (shown more clearly in FIG. 2B). The sensing region 204a of the working electrode 204 may also generally contain somatic cells 208 which are immobilized, as discussed above in reference to FIGS. 1A and 1B, either before or after being formed over the sensing region 204a of the working electrode. As shown in FIG. 2A, the somatic cells 208 may generally cover at least a portion of the sensing region 204a, such that the sensing portion may provide an output measurement in response to a change in the somatic cells 208. Furthermore, both electrode 204 and reference electrode 206 may be formed as discussed in regards to FIGS. 1A and 1B, and thus, may optionally include one or more adhesive layers.

The TEER biosensor 200 may also generally include a case 212 which includes a channel 214, and one or more inlets 216 and outlets 218, for introducing and removing a sample from the case 212. In one aspect, the one or more inlets 216 and outlets 218 may have any shape as known in the art. However, in an aspect, the one or more inlets 216 and outlets 218 may have a conical or tapered shape. Moreover, as shown in FIG. 2B, the case may be opaque and surround the working electrode 204 and reference electrode 206. Therefore, in an aspect such as shown in FIGS. 2A and 3B, visual observations and measurements may not be conducted, and only the electrical measurements may be relied upon.

Figure 3A:
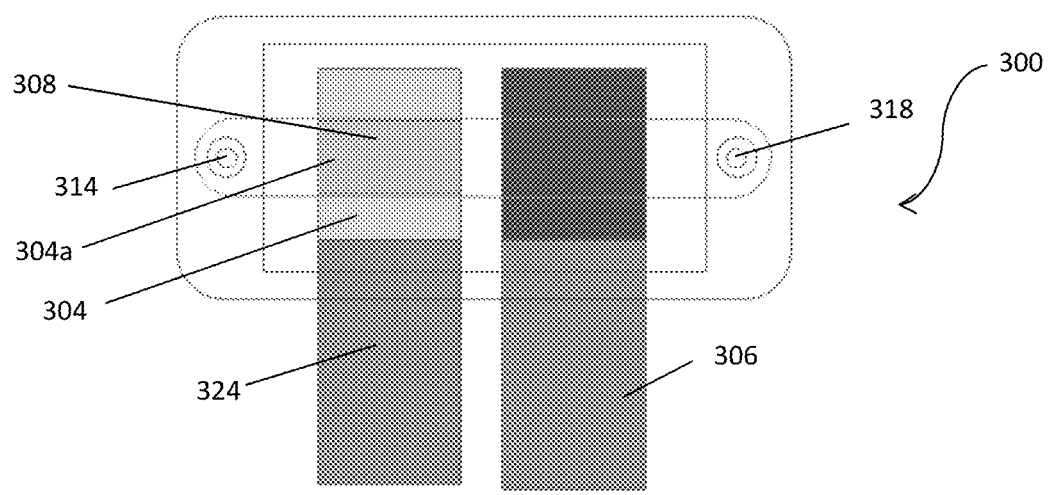
FIG. 3A illustrates a top view of a TEER biosensor according to the present disclosure.
Figure 3B:
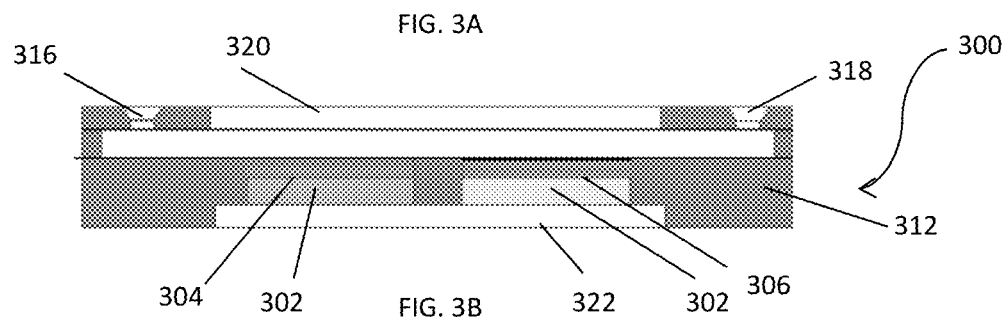
FIG. 3B illustrates a cross-section of the TEER biosensor of FIG. 3A.

Now referring to FIGS. 3A and 3B, a further aspect of a TEER biosensor 300 according to the present disclosure may include an electrode 304 that is formed from graphene. As discussed above, the graphene electrode may be somewhat transparent, allowing the working electrode and somatic cells to be visible during sensing. Therefore, in one aspect, the case 312 maybe at least partially formed from a transparent material. For instance, as shown in an aspect according to FIG. 3B, glass or plastic, such as polycarbonate, observation covers 320 and 322 may be used to provide visibility to the working electrode 304. Of course, it should be understood that, as the electrodes are measuring the change in resistance, visibility is not necessary in order to conduct the test, and thus, a graphene electrode may be placed in an opaque case.

Nonetheless, as shown in FIGS. 3A and 3B, while the sensing portion 304a of the working electrode 304 may be formed from graphene, the substrate 302 (shown more clearly in FIG. 3B) may include a partial gold contact 324 on a portion of the substrate, spaced apart from the sending region 304a. Therefore, it should be understood that, the present disclosure also contemplates an gold/graphene electrode, as well as a gold functionalized glass substrate.

Figure 4A:
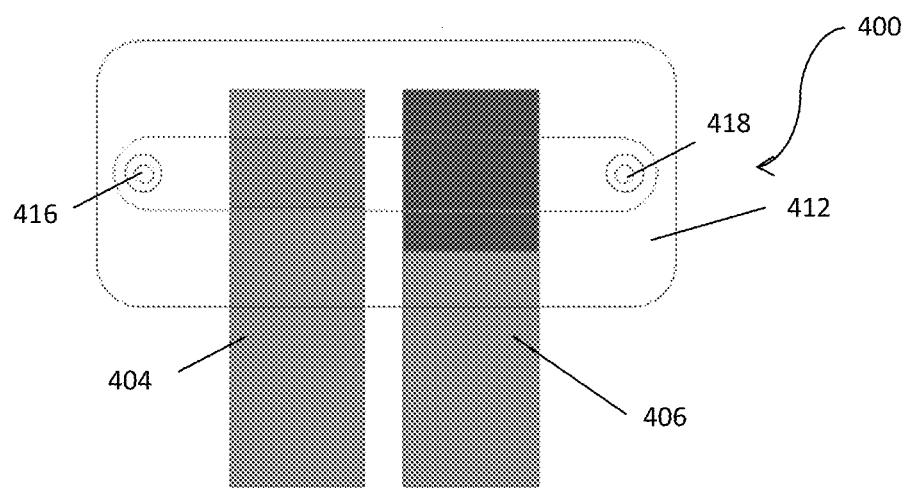
FIG. 4A illustrates a top view of a TEER biosensor according to the present disclosure.
Figure 4B:
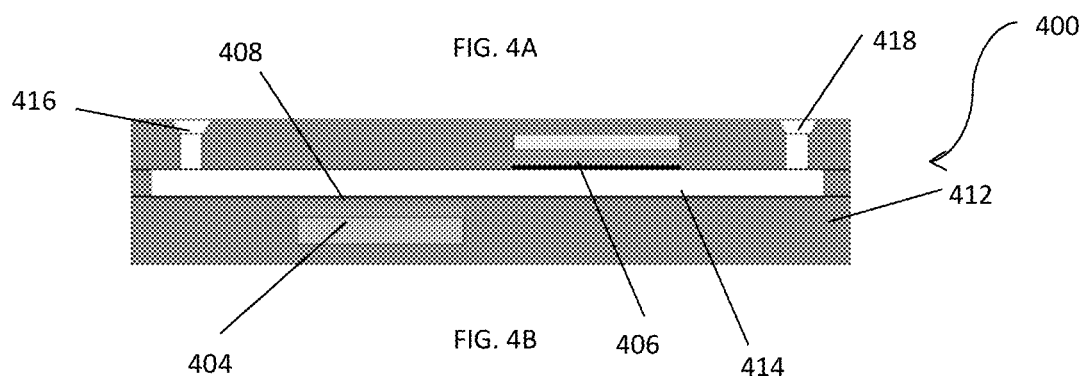
FIG. 4B illustrates a cross-section of the TEER biosensor of FIG. 4A.

Furthermore, an additional aspect according to the present disclosure may be shown by FIGS. 4A and 4B, in which the reference electrode 406 is located on an opposite side of the channel 414 from the working electrode 404, in an inverted configuration. Thus, in such an aspect, the working electrode 404 may be located on a first side of the channel 414, and the reference electrode 406 may be located on a second side of the channel 414 (shown more clearly in FIG. 4B). While not shown, it should also be understood that the reference electrode 406, or the working electrode 404, may be inverted directly above the other (e.g., in FIG. 4B, the reference electrode 406 would be inverted directly across the channel 414 from the working electrode 404, such that the reference electrode 406 was located directly over the somatic cells 408). By using such a configuration, a compact and space efficient biosensor may be formed while still maintaining excellent detection properties.

Throughout the figures and discussion, the case, electrode, and reference electrode have been referred to and shown as having a rectangular or quadrilateral shape. However, while not shown, it should be understood that the case, electrode, or reference electrode, may have any shape as is known in the art.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A biosensor for detecting transepithelial/transendothelial electrical resistance comprising:
   at least one substrate;
   an adhesion layer that overlies the at least one substrate, wherein the adhesion layer includes tantalum, chromium, tantalum nitride, tungsten-titanium, titanium, titanium nitride, or a combination thereof;
   a working electrode that overlies the adhesion layer and is formed on at least a portion of the at least one substrate, the working electrode comprising a biologically inert material, wherein the biologically inert material includes gold, graphene, carbon nanotubes, or a combination thereof;
   a reference electrode that overlies the adhesion layer and is formed on the at least one substrate; and
   a case, wherein the case defines side walls, a lower wall, and a channel, wherein the channel has a volume of about 150 microliters or less and contacts the working electrode, further wherein the channel extends between at least one inlet and at least one outlet, the at least one inlet having a tapered and/or conical shape and the at least one outlet having a tapered and/or conical shape, further wherein the at least one inlet and the at least one outlet have an innermost part and an outermost part, the outermost part of the at least one inlet and the at least one outlet having a larger diameter than the innermost part of the at least one inlet and the at least one outlet;
   wherein the adhesion layer is positioned between the at least one substrate and the working electrode and/or the reference electrode;
   wherein spino-cerebral endothelial cells are immobilized with at least one linking agent, wherein the at least one linking agent comprises a thiol, a pyrene, a diazonium, an azide, a sol-gel, or a combination thereof, and further wherein the at least one linking agent continuously covers a portion of a top surface of the working electrode, a side surface of the working electrode, and a portion of a top surface of the at least one substrate;
   further wherein at least the portion of the working electrode wherein the spino-cerebral endothelial cells are immobilized is transparent having a percent transmittance of at least 80% but no more than about 99.9%; and
   wherein the biosensor is configured to detect a first resistance measurement and a second resistance measurement, wherein the spino-cerebral endothelial cells are immobilized on the portion of the top surface of the working electrode during both the first resistance measurement and the second resistance measurement.

2. The biosensor according to claim 1, wherein the working electrode is formed on a first substrate of the at least one substrate and the reference electrode is formed on a second substrate of the at least one substrate.

3. The biosensor according to claim 1, wherein the at least one substrate comprises glass, silicone, or a polymer.

4. The biosensor according to claim 1, wherein at least a portion of the case is transparent.

5. The biosensor according to claim 1, further comprising a second working electrode and a second reference electrode.

6. A method of detecting a change in transepithelial/transendothelial electrical resistance of spino-cerebral endothelial cells comprising:
   providing a biosensor having:
      at least one substrate;
      an adhesion layer that overlies the at least one substrate, wherein the adhesion layer includes tantalum, chromium, tantalum nitride, tungsten-titanium, titanium, titanium nitride, or a combination thereof;
      a working electrode that overlies the adhesion layer and is formed on at least a portion of the at least one substrate, the working electrode comprising a biologically inert material;
      a reference electrode that overlies the adhesion layer and is formed on the at least one substrate; and
      a case, wherein the case defines side walls, a lower wall, and a channel, wherein the channel has a volume of about 150 microliters or less and contacts the working electrode, further wherein the channel extends between at least one inlet and at least one outlet, the at least one inlet having a tapered and/or conical shape and the at least one outlet having a tapered and/or conical shape, further wherein the at least one inlet and the at least one outlet have an innermost part and an outermost part, the outermost part of the at least one inlet and the at least one outlet having a larger diameter than the innermost part of the at least one inlet and the at least one outlet;
      wherein the adhesion layer is positioned between the at least one substrate and the working electrode and/or the reference electrode;
      wherein the spino-cerebral endothelial cells are immobilized with at least one linking agent, wherein the at least one linking agent comprises a thiol, a pyrene, a diazonium, an azide, a sol-gel, or a combination thereof, and further wherein the at least one linking agent continuously covers a portion of a top surface of the working electrode, a side surface of the working electrode, and a portion of a top surface of the substrate, and further wherein at least the portion of the working electrode wherein the spino-cerebral endothelial cells are immobilized is transparent having a percent transmittance of at least 80% but no more than about 99.9%;

conducting a first resistance measurement by measuring a voltage at the working electrode across the spino-cerebral endothelial cells;

contacting the working electrode with a biological sample; and conducting a second resistance measurement by measuring the voltage at the working electrode across the spino-cerebral endothelial cells.

7. The method of claim 6, wherein the biological sample has a volume of about 1 μL to about 500 μL.

8. The method of claim 7, wherein the biological sample has a volume of about 15 μL to about 100 μL.

9. The method of claim 6, wherein the biological sample is mammalian spino-cerebral fluid or blood serum.

10. The method of claim 6, wherein the biological sample is introduced into the biosensor via the at least one inlet.

\* \* \* \* \*